(12) United States Patent
Takada et al.

(10) Patent No.: US 6,607,743 B1
(45) Date of Patent: Aug. 19, 2003

(54) BONE RESORPTION SUPPRESSING AGENT

(75) Inventors: Yukihiro Takada, Kawagoe (JP); Atsushi Serizawa, Kawagoe (JP); Hidetoshi Ishikawa, Sapporo (JP); Tomoe Yoshioka, Ebetsu (JP); Seiichiro Aoe, Sayama (JP)

(73) Assignee: Snow Brand Milk Products Co., Ltd., Hokkaido (JP)

( * ) Notice: Subject to any disclaimer, the term of this patent is extended or adjusted under 35 U.S.C. 154(b) by 0 days.

(21) Appl. No.: 09/537,468

(22) Filed: Mar. 24, 2000

(30) Foreign Application Priority Data

Mar. 30, 1999 (JP) .......................... 11-089946

(51) Int. Cl.$^7$ .............................. A61K 47/00
(52) U.S. Cl. ...................... 424/439; 424/400; 424/440; 424/451; 424/464
(58) Field of Search ............... 424/439, 440, 424/400, 464, 451

(56) References Cited

U.S. PATENT DOCUMENTS

| | | | | | |
|---|---|---|---|---|---|
| 4,701,329 A | * | 10/1987 | Nelson et al. | ................ | 426/74 |
| 5,514,382 A | * | 5/1996 | Sultenfuss | ................ | 424/440 |
| 5,985,335 A | * | 11/1999 | Dietl | ................ | 424/610 |

FOREIGN PATENT DOCUMENTS

| | | | | | |
|---|---|---|---|---|---|
| EP | 0373711 A2 | * | 6/1990 | ........ | A61K/37/64 |
| EP | 0 373 771 A2 | | 6/1990 | | |
| JP | 07 002896 | | 1/1995 | | |
| JP | 07002896 | * | 1/1995 | ........ | C07K/14/51 |
| JP | 10 080281 | | 3/1998 | | |
| WO | WO 97/14797 | | 4/1997 | | |

OTHER PUBLICATIONS

Magnus Abrahamson, et al., Isolation of Six Cysteine Proteinase Inhibitors from Human Urine. Their Physicochemical and Enzyme Kinetic Properties and Concentrations in Biological Fluids., The Journal of Biological Chemistry vol. 261, No. 24, 1986, pp. 11282–11289.

* cited by examiner

Primary Examiner—Thurman K. Page
Assistant Examiner—Robert M. Joynes
(74) Attorney, Agent, or Firm—Knobbe, Martens Olson & Bear LLP

(57) ABSTRACT

A highly safe bone resorption suppressing agents, which can be used as medicines or admixed to food products or feeds, is produced. Milk-derived basic cystatins and/or milk-derived basic cystatin decomposition products prepared from milk are made into bone resorption suppressing agents, or admixed to drinks, food products and feeds.

7 Claims, No Drawings

BONE RESORPTION SUPPRESSING AGENT

BACKGROUND OF THE INVENTION

1. Field of the Invention

The present invention relates to bone resorption suppressing agents comprising a milk-derived basic cystatin and/or milk-derived basic cystatin decomposition product as an effective component, and in particular to bone resorption suppressing agents to be used for the prevention and treatment of bone joint diseases or periodontal diseases.

The present invention also relates to drinks, food products and feed in which a milk-derived basic cystatin and/or milk-derived basic cystatin decomposition product are admixed to provide an activity to prevent and treat bone joint diseases or periodontal diseases. In particular, the present invention relates to drinks, food products and feed to which a highly absorbable calcium composition and vitamin D and/or vitamin K, in addition to a milk-derived basic cystatin and/or milk-derived basic cystatin decomposition product, are admixed to provide an activity to prevent and treat bone joint diseases or periodontal diseases.

2. Description of the Related Art

In recent years, the number of people suffering from bone joint diseases such as osteoporosis and rheumatism has been on the rise because of the aging population. Bone formation and bone resorption continuously take place in bone tissue and are well balanced in early life, but the balance is lost with an increase in bone resorption with aging for various reasons. If this unbalance continues for a long period of time, the bone tissue becomes fragile, which results in bone diseases such as osteoporosis, bone fractures and lumbago. It is believed that if this uncoupling can be prevented, osteoporosis, bone fractures, lumbago or the like can be prevented.

Conventional methods to prevent and treat bone diseases by preventing the uncoupling include (1) dietary supplementation of calcium, (2) moderate exercise, (3) sunbathing, and (4) therapy by medicines.

For dietary supplementation, calcium salts such as calcium carbonate and calcium phosphate, natural calcium supplements such as bovine bone powders, egg shells and fish bone powders are used. To date, such food products and food materials have been used exclusively for calcium supplementation.

For moderate exercise, moderate running or walking are highly recommended. However, even moderate exercise is difficult for people who are physically weak and, not to mention, almost impossible for elderly people who are confined to bed.

Sunbathing is good for the supplementation of activated vitamin $D_3$, but not sufficient by itself.

As for therapeutic medicines, 1α-hydroxy vitamin $D_3$, calcitonin preparations or the like are known to be effective to cure and treat osteoporosis. Calcitonin preparations are medicinal hormone preparations. Safe substances for calcitonin obtainable from food materials have not been presently studied. Calcitonin is difficult to prepare in bulk and to provide as a safe food material since animal tissues, cells, blood, or urine have to be used as raw materials.

It is believed that rheumatism, a joint disease, can be prevented and treated by suppressing bone resorption since it is associated with the bone resorption.

In recent years, periodontal diseases have also become a serious social problem. Unlike dental caries, periodontal diseases weaken the roots of teeth, which makes even healthy teeth useless. Today, many people develop symptoms of periodontal diseases. Periodontal diseases can be more serious than dental caries.

Today, means to prevent periodontal diseases are to prevent the growth of causative microorganisms, for example, the removal of dental plaque or gargling using mouthwashes containing antibacterial agents or the like. However, these means seem to be less effective for highly developed symptoms. Namely, in the late stage of periodontal diseases, the alveolar bone mass decreases, and once alveolar bones are lost, unregenerable symptoms occur. Teeth loss due to periodontal diseases then makes eating difficult and painful, which is disturbing in everyday life. Thus, there is a need for effective means for the prevention and treatment of periodontal diseases.

However, so far, there is no agent available for the prevention and treatment of periodontal diseases which effectively suppresses a decrease in alveolar bone mass.

Thus, like osteoporosis, periodontal diseases have become a serious social problem. Therefore, an effective treatment for periodontal diseases is will greatly contribute to people's health, and accordingly is necessary,.

The present inventors intensively searched for a milk whey fraction having osteoblast growth stimulating activity, bone resorption suppressing activity and bone strengthening activity, in order to obtain a material which can be used for the prevention and treatment of bone junction diseases and periodontal diseases. Namely, the present inventors fractionated proteins in milk, in particular milk whey, in an attempt to obtain a fraction having a bone resorption suppressing activity, and found a bone strengthening activity in a protein-peptide mixture which was obtained by treating a water soluble fraction of whey proteins with a reverse osmotic membrane or electrodialysis to remove whey-derived salts (Japanese Patent Laid-open No. 4-183371). Furthermore, the present inventors found that a fraction obtained by treating an aqueous solution of this protein-peptide mixture with ethanol, heat, salts or an ultrafiltration membrane has a bone strengthening activity (Japanese Patent Laid-open No. 5-176715, Japanese Patent Laid-open No. 5-320066). The present inventors also found that basic proteins present in milk in trace amounts have an osteoblast collagen synthesis stimulating activity and bone resorption suppressing activity (Japanese Patent Laid-open No. 8-151331).

Cystatin is a cysteine protease inhibitor which inhibits proteolytic activity of cysteine proteases having an SH group in the active center and is found in animal tissues, cells and urine. A virus growth inhibiting activity was recognized as a useful activity of cystatin (Biochem. Biophys. Res. Commun., Vol. 127, p. 1072, 1985).

Japanese Patent Laid-open No. 2-223529 describes the use of cystatin as anti-allergic agents and as therapeutic agents for bone diseases in the form of an injectable preparation, suppository, nasal powder or the like. More specifically, it described a test result wherein the blood calcium level was reduced in rats by intravenously injecting rats with rat-derived cystatin prepared by genetic engineering. However, one cannot readily conclude that cystatin has an activity to prevent and treat bone joint diseases such as osteoporosis and rheumatism, solely from this result.

Furthermore, until now, a bone resorption suppressing agent comprising a milk-derived basic cystatin and/or milk-derived basic cystatin decomposition product which is effective by administration orally but not necessarily intravenously, as an effective component, are not known.

Also, a drink, food product or feed which contains such components in higher concentrations, along with calcium and vitamins, and can be administered orally is not known.

Although the present inventors previously applied for a patent (Japanese Patent Laid-open No. 7-126294) on a cysteine protease inhibitor other than the milk-derived basic cystatin, the bone resorption suppressing activity of the milk-derived basic cystatin of the present invention is higher than that of said inhibitor.

SUMMARY OF THE INVENTION

The present inventors tried to isolate and purify an active substance from of basic protein fraction having a bone resorption suppressing activity, identified the resulting substance, and found this substance is a milk-derived basic cystatin. Furthermore, the present inventors found that the milk-derived basic cystatin has a particularly high bone resorption suppressing activity as compared with cystatins from other origins. Further, the present inventors found that a decomposition product of the milk-derived basic cystatin also has a high bone resorption suppressing activity, and thus completed the present invention.

Accordingly, the objective of the present invention is to provide bone resorption suppressing agents comprising the milk-derived cystatin and/or milk-derived cystatin decomposition product as an effective component, and drinks, food products and feeds in which the milk-derived cystatin and/or milk-derived cystatin decomposition product are admixed to provide a bone resorption suppressing activity.

Further, the present invention is industrially useful because a highly safe milk-derived basic cystatin can be prepared in bulk from a food material, i.e., milk, and admixed as a safe food material.

The present inventors found that a milk-derived basic cystatin and a milk-derived basic cystatin decomposition product have an excellent bone resorption suppressing activity and thus completed the present invention. Namely, the present invention provides bone resorption suppressing agents comprising the milk-derived basic cystatin and/or milk-derived basic cystatin decomposition product as an effective component. Further, the present invention can provide a bone resorption suppressing activity to drinks, food products and feed by admixing them with the milk-derived basic cystatin and/or milk-derived basic cystatin decomposition product. Further, the present invention can provide both a bone resorption suppressing activity and bone formation stimulating activity to drinks, food products and feed by admixing them with the milk-derived basic cystatin and/or milk-derived basic cystatin decomposition product with a highly absorbable calcium component and vitamin D and/or vitamin K.

More specifically, based on the above mentioned bone resorption suppressing activity of the milk-derived basic cystatin and/or milk-derived basic cystatin decomposition product, bone resorption suppressing agents can be provided, which comprises milk-derived basic cystatin and/or milk-derived basic cystatin decomposition product as an effective component for the prevention and treatment of bone joint diseases or periodontal diseases. Also, drinks, food products and feeds having activities to prevent and treat bone joint diseases or periodontal diseases can be provided by admixing them with milk-derived basic cystatin and/or milk-derived basic cystatin decomposition products.

The present invention provides a bone resorption suppressing activity to drinks, food products and feed by admixing the safe milk-derived basic cystatin and/or milk-derived basic cystatin decomposition product prepared using cow's milk, a food product, as a raw material.

DETAILED DESCRIPTION OF THE PREFERRED EMBODIMENT

Examples of milk to be used as a raw material for the milk-derived basic cystatin include raw milk, powdered milk, skimmed milk, and reconstituted milk. The milk-derived basic cystatin can be obtained from these milk materials by heating, salt treatment, ethanol treatment, various chromatographic methods, such as ion exchange chromatography and gel filtration chromatography, treatment with an ultrafiltration membrane, or the like.

A milk-derived basic cystatin decomposition product of the present invention is a peptide mixture prepared by restrictively decomposing the abovementioned milk-derived basic cystatin with proteases, such as trypsin, chymotrypsin, pepsin, papain, kallikrein, cathepsin, thermolysin, and B8 protease.

In the present invention, the abovementioned milk-derived basic cystatin and/or milk-derived basic cystatin decomposition product are added to drinks and food products to provide them with bone resorption suppressing activity. Examples of such drinks and food products include milk, milk drinks, juices, jellies, biscuits, breads, noodles, and sausages. Bone joint diseases, such as osteoporosis and rheumatism, and periodontal diseases can be prevented or treated by ingesting such drinks and food products to which the bone resorption suppressing activity is provided.

In the present invention, a milk-derived basic cystatin and/or milk-derived basic cystatin decomposition product are used as medicines, or admixed into drinks, food products and feed as an effective component for the prevention or treatment of bone joint diseases, such as osteoporosis and rheumatism, in an amount of about 8 $\mu$g to 10 mg per day for an adult, to be administered in divided doses. In particular, the milk-derived basic cystatin and/or milk-derived basic cystatin decomposition product are preferably admixed into drinks, food products or feed, at a concentration of more than 4 $\mu$g % so as to easily attain the above-mentioned dosage.

In the present invention, a milk-derived basic cystatin and/or milk-derived basic cystatin decomposition product are used as medicines, or admixed into drinks, food products and feed as an effective component for the prevention or treatment of periodontal diseases, for example in a form of tooth paste, mouth wash, candy, chewing gum or troche by bringing them into contact with the tooth surface in an amount of about 8 $\mu$g to 10 mg per day for an adult to be administered in divided doses.

A highly absorbable calcium salt having an excellent absorbability is preferably admixed into bone resorption suppressing agents, drinks, food products and feed of the present invention. Examples of the highly absorbable calcium salt include calcium chloride, calcium carbonate, calcium lactate, egg shells and substances containing milk-derived calcium. Effective components for bones, such as vitamin D and vitamin K, can also be admixed. In such cases, the desirable synergistic effect of the bone formation stimulating activity provided by admixing the abovementioned highly absorbable calcium and vitamins with the bone resorption suppressing activity provided by a milk-derived basic cystatin and/or milk-derived basic cystatin decomposition product can be attained.

Milk-derived basic cystatin has bone resorption suppressing activity when ingested as an admixture in food products

EXAMPLE 1

Preparation of Milk-derived Basic Cystatin

A column filled with S-Sepharose (3,000 g) was thoroughly washed with deionized water. Skimmed milk (10,000 L) was passed through the column, the column was thoroughly washed with deionized water, then elution was carried out with a linear concentration gradient of 0.1 to 1.0 M sodium chloride. The eluted fraction was heated at 90C for 10 minutes and centrifuged to remove precipitates. Next, the resulting fraction containing milk-derived basic cystatin was again fractionated using MonoS ion exchange chromatography. The fraction thus obtained was fractionated using MonoQ ion exchange chromatography and Superose 12 gel filtration chromatography using an HPLC system, they further by hydroxyapatite chromatography, and C4 reverse phase chromatography using an HPLC system to obtain a milk-derived basic cystatin (fraction A, 58 mg).

EXAMPLE 2

Preparation of Milk-derived Basic Cystatin

A 5% milk whey protein solution (10,000 L) was heated at 90C for 10 minutes and centrifuged to remove precipitates. A column was filled with a carrier, in which carboxymethylated papain was bound to Tresyl-Toyopearl (a product of Toso), and equilibrated with a 0.5 M sodium chloride solution. The resulting solution was passed through this column, after which the column was washed with a 0.5 M sodium chloride solution, then a 0.5 M sodium chloride solution containing 0.1% Tween 20. Next, cysteine protease was eluted with a 20 mM acetic acid-0.5 M sodium chloride solution. The eluted fraction was immediately neutralized with a 1 M sodium hydroxide solution, then fractionated on MonoS anion exchange chromatography, then hydroxy apatite chromatography and C4 reverse phase chromatography using an HPLC system to obtain a milk-derived basic cystatin (fraction B, 48 mg).

EXAMPLE 3

Preparation of Milk-derived Basic Cystatin Decomposition Product

Fraction A (25 mg) obtained in Example 1 was suspended in 100 ml of water, pancreatin was added at a final concentration of 1%, and enzyme treatment was carried out at 37C for 5 hours. Then, the enzyme was inactivated by heating at 90C for 5 minutes, after which the resulting substance was freeze-dried to obtain a milk-derived basic cystatin decomposition product (fraction C, 23 mg).

Fraction B (25 mg) obtained in Example 2 was similarly treated to obtain a milk-derived basic cystatin decomposition product (fraction D, 24 mg).

TEST EXAMPLE 1

Bone Resorption Suppressing Activity of Milk-derived Basic Cystatins and Milk-derived Basic Cystatin Decomposition Products Splint bones of ICR mice (10–20 days of age) were taken out, soft tissues were removed, then the bones were mechanically ground in an α-MEM solution containing 5% fetal calf serum to obtain whole bone cells including osteoclasts. These cells (about $2\times10^6$) were spotted on an ivory piece using an α-MEM solution containing 5% fetal calf serum. After several hours, an α-MEM solution containing 5% fetal calf serum, to which a milk-derived basic cystatin or a milk-derived basic cystatin decomposition product was added at a concentration of 50 ng/ml, was added to the spot, and the ivory piece was incubated in the presence of 5% $CO_2$ at 37C for 5 days to examine bone resorption activity of osteoclasts.

After incubation, cells on the ivory piece were pealed, stained with hematoxylin, and subjected to image analysis using an image analyzing device (PIASLA-555, a product of PIAS) to count the number of bone resorption pits. The bone resorption activity (%) as defined in the following formula is obtained from the counts to evaluate the bone resorption suppressing activity.

Bone resorption activity (%)=(bone resorption pit count for group with added test sample/bone resorption pit count for group without added test sample)×100.

Test samples used were milk-derived basic cystatins and milk-derived basic cystatin decomposition products (fractions A to D) obtained in Examples 1, 2 and 3, and the following non-milk origin cystatins, and a milk-derived cysteine protease inhibitor.

1. Cystatin (egg white; purity more than 99%)
2. Cystatin (human placenta; purity more than 99%)
3. Cystatin (human plasma; purity more than 99%)
4. Cystatin (bovine urine; purity more than 99%)
5. Cystatin (bovine plasma; purity more than 99%)
6. Cysteine protease inhibitor (see Japanese Patent Laid-open No. 95-126294) (bovine milk; purity more than 99%)

Results are shown in Table 1. Bone resorption activity was suppressed better in cells cultured in a medium supplemented with milk-derived basic cystatins or milk-derived basic cystatin decomposition products than in cells cultured in a medium without these supplements. Further, milk-derived basic cystatins and milk-derived basic cystatin decomposition products (fractions A to D) showed marked bone resorption suppressing activity as compared with cystatins of other origins, and thus an excellent bone resorption suppressing activity of milk-derived basic cystatins was confirmed.

TABLE 1

| Test sample | Bone resorption activity (% ± SD) |
|---|---|
| Fraction A | 44.2 ± 6.9 |
| Fraction B | 55.8 ± 5.2 |
| Fraction C | 32.5 ± 5.6 |
| Fraction D | 41.3 ± 4.7 |
| Cystatin (egg white) | 75.1 ± 3.5 |
| Cystatin (human placenta) | 78.1 ± 2.9 |
| Cystatin (human plasma) | 79.5 ± 1.9 |
| Cystatin (bovine urine) | 77.2 ± 3.7 |
| Cystatin (bovine plasma) | 68.7 ± 3.3 |
| Cysteine protease inhibitor (bovine milk) | 64.3 ± 2.5 |

TEST EXAMPLE 2

Bone Resorption Suppressing Activity and Bone Strengthening Activity of Milk-derived Basic Cystatin and Milk-derived Basic Cystatin Decomposition Product Fractions A and C obtained in Examples 1 and 3, respectively, were administered to osteoporosis model rats to study their effect on bone resorption suppression.

Feeds used for the administration test were a feed admixed with fraction A or fraction C and a feed admixed with fraction A or fraction C, a highly absorbable milk-derived calcium component (milk Ca, see Japanese Patent Laid-open No. 1992-306622) as a calcium source, and 200 IU of vitamin D.

Compositions of the feeds used in the administration test are shown in Table 2. The amount of both calcium and phosphate was 300 mg per 100 g feed in all test groups so that a calcium to phosphate ratio was 1:1.

TABLE 2

|  | Control | Sham | Fraction A | Fraction C | Fraction + Milk Ca[2] + VD[3] A | Fraction + Milk Ca[2] + VD[3] C |
|---|---|---|---|---|---|---|
| Sucrose | 50.0 | 50.0 | 50.0 | 50.0 | 50.0 | 50.0 |
| Casein | 20.0 | 20.0 | 18.0 | 18.0 | 18.0 | 18.0 |
| Cornstarch | 15.0 | 15.0 | 15.0 | 15.0 | 15.0 | 15.0 |
| Cellulose | 5.0 | 5.0 | 5.0 | 5.0 | 5.0 | 5.0 |
| Corn oil | 5.0 | 5.0 | 5.0 | 5.0 | 5.0 | 5.0 |
| Vitamin mixture (including choline) | 1.2 | 1.2 | 1.2 | 1.2 | 1.2 | 1.2 |
| Mineral mixture | 4.5[1] | 4.5[1] | 4.5[1] | 4.5[1] | 4.5[2] | 4.5[2] |
| Fraction A | — | — | 0.0004 | — | 0.0004 | — |
| Fraction C | — | — | — | 0.0004 | — | 0.0004 |

(Units: g/100 g)

1) Calcium carbonate was admixed as a calcium source.
2) Milk-derived calcium component was admixed as a calcium source.
3) 200 IU of vitamin D were admixed.

Female SD rats (32 weeks of age) were used for experimental animals. After preliminary rearing for one week, an ovariectomy was performed, then the rats were reared further for 2 weeks on a low calcium diet to create osteoporosis model rats. Sham operations without an ovariectomy were performed on 7 rats to make sham rats.

The abovementioned rats were divided into six groups (7 rats in one group), i.e., control group, sham group, fraction A group, fraction C group, fraction A+milk calcium+vitamin D group, and fraction C+milk calcium+vitamin D group, and rats in each group were fed the test feeds shown in Table 2, for one month.

After administering the test feeds, thigh bones of rats in each test group were removed, the amount of bone mineral was measured by a bone mineral measuring device, and the bone strength was measured by a tension fracture characteristic measuring device.

Results are Shown in Table 3 and Table 4.

As shown in Table 3, the amount of bone mineral was statistically greater in animals fed the feed admixed with faction A or fraction C as compared to those in the control group. Accordingly, it was revealed that fraction A and fraction C had bone resorption suppressing activity. The activity was further augmented by the addition of highly absorbable milk calcium and vitamin D.

As shown in Table 4, the bone strength was statistically higher in animals fed the feeds admixed with fraction A or fraction C than in the control animals. Accordingly, it was revealed that fraction A and fraction C had bone strengthening activity. Further, the activity was further augmented by the addition of highly absorbable milk calcium and vitamin D.

A similar result was obtained with the feed admixed with vitamin K instead of vitamin D.

The abovementioned results showed that the milk-derived basic cystatin and milk-derived basic cystatin decomposition product had bone resorption suppressing activity and bone strengthening activity.

TABLE 3

|  | Bone mineral (mg, ±SD) |
|---|---|
| Sham | 136.2 ± 6.3* |
| Control | 116.3 ± 5.9 |
| Fraction A | 122.4 ± 4.3* |
| Fraction C | 123.8 ± 5.1* |
| Fraction A + milk Ca + vitamin D | 126.1 ± 2.9* |
| Fraction C + milk Ca + vitamin D | 127.3 ± 3.1* |

*Significantly different from the control group ($p < 0.05$)

TABLE 4

|  | Bone breaking energy ($\times 10^5$ erg) |
|---|---|
| Sham | 13.4 ± 2.6* |
| Control | 8.3 ± 1.7 |
| Fraction A | 10.8 ± 3.1* |
| Fraction C | 10.5 ± 4.1* |
| Fraction A + milk Ca + vitamin D | 11.3 ± 2.3* |
| Fraction C + milk Ca + vitamin D | 11.5 ± 2.6* |

*Significantly different from the control group ($p < 0.05$)

TEST EXAMPLE 3

The ingredients shown in Table 5 were mixed, poured into containers and sterilized by heating to prepare drinks. Albumin was added to a control group to adjust the amount of proteins.

Twenty patients having osteoarthritis (shrinkage of joint cleavage) were divided into two groups with 10 patients in each group, and took the drinks for one month. The amount of urinary deoxypyridinoline, a bone metabolism marker for bone resorption, was measured before and after the period of drinking.

Results are shown in Table 6 and Table 7. As shown in Table 6, while the amount of deoxypyridinoline was reduced even in the control group having the drink with calcium and vitamin, it was reduced further more in the test group. This result suggests that bone resorption due to bone fracture was well suppressed. As shown in Table 7, various joint pains were also reduced by the intake of the drink. Furthermore, similar results were obtained by using cheese in which a milk-derived basic cystatin was admixed.

TABLE 5

| Ingredients | Control group | Test group |
|---|---|---|
| Crystalline glucose | 15.0 | 15.0 (% by weight) |
| Fraction A |  | 0.000008 |
| Albumin | 0.000008 |  |
| Calcium | 0.5 | 0.5 |
| Vitamin D | (200 IU) | (200 IU) |
| Water | 74.0 | 74.0 |

TABLE 6

| Reduction amount of deoxypyridinoline (nmol/day, ±SD) | |
|---|---|
| Control group | 0.32 ± 0.3 |
| Test group | 0.99 ± 0.2* |

*Significantly different from the control group ($p < 0.05$).

TABLE 7

| | Number of patients | | | |
| --- | --- | --- | --- | --- |
| | Control group | | Test group | |
| | Before intake | After intake | Before intake | After intake |
| Physically strained joint pain | 10 | 10 | 10 | 8 |
| Joint pain with motion | 5 | 5 | 6 | 2 |
| Joint pain while asleep | 5 | 4 | 5 | 0 |
| Joint pain in exhaustion | 8 | 8 | 9 | 5 |
| Fatigue | 7 | 7 | 6 | 1 |
| Joint painat the entire cleavage | 9 | 8 | 9 | 3 |

TEST EXAMPLE 4

Forty-eight golden hamsters (6 weeks of age) were preliminarily reared for one week, after which a sterilized silk suture No. 4 was coiled in five-ply around the M1 column dentis of each animal, and the animals were reared by feeding the feed of Keyes et al. (D#2000, Keyes, P. H. and Jordan: Archs. Oral. Biol., 9, 377–400, 1964) to induce periodontal diseases. Next, the resulting golden hamsters were divided into four groups, i.e., control group, fraction A group, fraction B group, and fraction C group. A test solution was prepared by appropriately diluting each fraction (4 μg) and applied to the animals of each group 2 times a day every day, keeping the inside the oral cavity of the animals wet for about 10 minutes each time. Six animals of each group were selected 4 and 7 days after the application, both sides of lower jaw bones were excised after fixed perfusion with a 2.5% glutaraldehyde solution (pH 7.4) for about 20 minutes, then the reduction of alveolar bone mass was evaluated by the following method. Namely, both excised sides of lower bones were fixed with a 2.5% glutaraldehyde solution and soft-X-rayed, then the resulting photographs were analyzed using an image analyzing device (PIAS LA-555). The area between the enamel cement border and alveolar bone top near M1 was measured to evaluate the reduction in alveolar bone mass.

Results are shown in Table 8. Reduction in alveolar bone mass in the golden hamsters in fraction A group, fraction B group and fraction C group was significantly low as compared with that in the control group. Accordingly, it was revealed that the milk-derived basic cystatins and milk-derived basic cystatin product were effective in suppressing alveolar bone mass reduction and for preventing and treating periodontal diseases.

TABLE 8

| Reduction in area (mm$^2$) | Control | Fraction A | Fraction B | Fraction C |
| --- | --- | --- | --- | --- |
| Day 4 | 0.31 | 0.16* | 0.18* | 0.15* |
| Day 7 | 0.98 | 0.53* | 0.58* | 0.47* |

*Significantly different from the control group ($p < 0.05$).

EXAMPLE 4

Production of Drink to Which Bone Resorption Suppressing Activity was Provided The ingredients in Table 9 were mixed, fraction A (0.000004% by weight) and vitamin D (200 IU) were further added, then the admixture was poured into a container and sterilized by heating to produce a drink to which bone resorption suppressing activity was provided. This drink is useful for the prevention and treatment of bone joint diseases.

TABLE 9

| Mixed isomerized sugars | 15.0 (% by weight) |
| --- | --- |
| Fruit juice | 10.0 |
| Citric acid | 0.5 |
| Flavoring | 0.1 |
| Calcium | 0.5 |
| Water | 73.9 |

EXAMPLE 5

Production of Tablets to Which Bone Resorption Suppressing Activity was Provided The ingredients in Table 10 were mixed, fraction A (0.0005% by weight) and vitamin D (200 IU) were further added, then the admixture was molded under pressure to produce tablets to which bone resorption suppressing activity was provided. These tablets are useful for the prevention and treatment of bone joint diseases.

TABLE 10

| Hydrous crystalline glucose | 93.5 (% by weight) |
| --- | --- |
| Calcium | 5.0 |
| Sugar esters | 1.0 |
| Flavoring | 0.5 |

EXAMPLE 6

Production of Biscuits to Which Bone Resorption Suppressing Activity was Provided The ingredients of Table 11 were mixed, fraction B (0.00005% by weight) was further added, then the resulting dough was molded and baked to produce biscuits to which bone resorption suppressing activity was provided. These biscuits are useful for the prevention and treatment of bone joint diseases.

TABLE 11

| Flour | 50.0 (% by weight) |
| --- | --- |
| Sugar | 20.0 |
| Table salt | 0.5 |
| Margarine | 12.5 |
| Egg | 12.1 |
| Water | 4.1 |
| Sodium hydrogencarbonate | 0.1 |
| Ammonium bicarbonate | 0.2 |
| Calcium carbonate | 0.5 |

EXAMPLE 7

Production of Jelly to Which Bone Resorption Suppressing Activity was Provided The ingredients in Table 12 were mixed, fraction D (0.000008% by weight) was further added, then the admixture was poured into a container and sterilized by heating to produce jelly to which bone resorption suppressing activity was provided. This jelly is useful for the prevention and treatment of bone joint diseases.

TABLE 12

| | |
|---|---|
| Fructose | 20.0 (% by weight) |
| Granulated sugar | 15.0 |
| Starch syrup | 5.0 |
| Agar | 1.0 |
| Flavoring | 0.1 |
| Calcium | 0.1 |
| Water | 58.8 |

EXAMPLE 8

Production of Cheese to Which Bone Resorption Suppressing Activity was Provided

The ingredients in Table 13 were mixed, fraction A (0.00005% by weight) was further added, then the admixture was emulsified at an emulsifying temperature of 85C to produce cheese to which bone resorption suppressing activity was provided. This cheese is useful for the prevention and treatment of bone joint diseases.

TABLE 13

| | |
|---|---|
| Gouda cheese | 43.0 (% by weight) |
| Cheddar cheese | 43.0 |
| Sodium citrate | 2.0 |
| Milk-derived calcium | 1.0 |
| Water | 10.5 |

EXAMPLE 9

Production of Yoghurt to Which Bone Resorption Suppressing Activity was Provided Skim milk (12%) was pasteurized by heating at 90C for 20 minutes, and *Lactobacillus acidophilus* and *Streptococcus thermophilus* were individually inoculated to make two kinds of starter cultures. The ingredients in Table 12 including a yoghurt mix, whose major component is milk, were mixed, fraction B (0.000008% by weight) was further added, then the admixture was subjected to conventional fermentation and cooling to produce yoghurt to which bone-resorption suppressing activity was provided. This yoghurt is useful for the prevention and treatment of bone joint diseases.

TABLE 13

| | |
|---|---|
| Yoghurt mix | 97.0 (% by weight) |
| Culture (*L. acidophilus*) | 1.5 |
| Culture (*S. thermophilus*) | 1.5 |

EXAMPLE 10

Production of dog Food to Which Bone Resorption Suppressing Activity was Provided The ingredients in Table 15 were mixed, and fraction A (0.00001% by weight) was further added to produce a dog food to which bone resorption suppressing activity was provided. This dog food is useful for the prevention and treatment of bone joint diseases.

TABLE 15

| | |
|---|---|
| Soybean cake | 12.0 (% by weight) |
| Powdered skim milk | 14.0 |
| Soybean oil | 4.0 |
| Corn oil | 2.0 |
| Palm oil | 28.0 |
| Corn starch | 15.0 |
| Flour | 9.0 |
| Bran | 2.0 |
| Vitamin mixture | 9.0 |
| Mineral mixture | 2.0 |
| Cellulose | 3.0 |

EXAMPLE 11

Production of Tooth Paste to Which Bone Resorption Suppressing Activity was Provided The ingredients in Table 16 were mixed, fraction C (0.0001% by weight) was further added, the admixture was made into a cream and poured into a container to produce a tooth paste to which bone resorption suppressing activity was provided. This tooth paste is useful for the prevention and treatment of periodontal diseases.

TABLE 16

| | |
|---|---|
| Glycerine | 70.0 (% by weight) |
| Silicon dioxide | 20.0 |
| Xanthan gum | 1.0 |
| Mint flavoring | 1.0 |
| Titanium dioxide | 0.7 |
| Sodium fluoride | 0.3 |
| Distilled water | 7.0 |

EXAMPLE 12

Production of Gargle to Which Bone Resorption Suppressing Activity was Provided

The ingredients in Table 17 were mixed, and fraction B (0.00001% by weight) was further added to produce a gargle to which bone resorption suppressing activity was provided. This gargle is useful for the prevention and treatment of periodontal diseases.

TABLE 17

| | |
|---|---|
| Ethanol | 8.0 (% by weight) |
| Flavoring | 1.0 |
| Sorbitol | 5.0 |
| Propylene glycol | 5.0 |
| Distilled water | 81.0 |

EXAMPLE 13

Production of Chewing Gum to Which Bone Resorption Suppressing Activity was Provided The ingredients in Table 18 including a dissolved gum base were mixed and stirred, and fraction A (0.0001% by weight) was further added to produce a chewing gum to which bone resorption suppressing activity was provided. This chewing gum is useful for the prevention and treatment of periodontal diseases.

TABLE 18

| | |
|---|---|
| Gum base | 20.0 (% by weight) |
| Corn syrup | 10.0 |
| Dextrose monohydrate | 10.0 |
| Lactose | 5.0 |
| Glycerine | 5.0 |
| Sugar | 50.0 |

EFFECTIVENESS OF THE INVENTION

Bone resorption suppressing agents of the present invention comprising a milk-derived basic cystatin and/or milk-derived basic cystatin decomposition product as an effective component are useful as agents for the prevention and treatment of bone joint diseases or periodontal diseases.

Further, bone joint diseases or periodontal diseases can be prevented and treated by ingesting drinks, food products or feeds to which the milk-derived basic cystatin and/or milk-derived basic cystatin decomposition product of the present invention are admixed to provide bone resorption suppressing activity.

What is claimed is:

1. A bone resorption suppressing agent in unit dosage form, comprising a milk-derived basic cystatin decomposition product in an amount of 8 $\mu$g to 10 mg per said unit dosage from, and a carrier, said milk-derived basic cystatin decomposition product being an enzymatically decomposed product of a milk-derived basic cystatin.

2. The bone resorption suppressing agent as claimed in claim 1, wherein the enzymatically decomposed product is a protein product obtainable by (i) suspending a milk-derived basic cystatin in water; (ii) adding pancreatin to the suspension at a final concentration of 1%, (iii) carrying out enzyme treatment of the suspension; and (iii) inactivating the enzyme.

3. The bone resorption suppressing agent as claimed in claim 1 further comprising a highly absorbable calcium component, and Vitamin D and/or vitamin K.

4. A drink, human food product, or feed for non-human animals, comprising a milk-derived basic cystatin decomposition product, wherein more than 4 $\mu$g % by weight of said milk-derived basic cystatin decomposition product are admixed with said drink, human food product, or feed for non-human animals, said milk-derived basic cystatin decomposition product being an enzymatically decomposed product of a milk-derived basic cystatin.

5. The drink, food product, or feed as claimed in claim 4 wherein a highly absorbable calcium composition, and vitamin D and/or vitamin K are further admixed.

6. The drink, food product, or feed as claimed in claim 4 which comprises no less than 40 $\mu$% by weight of a milk-derived basic cystatin and/or milk-derived basic cystatin decomposition product.

7. The bone resorption suppressing agent as claimed in claim 1, wherein the milk-derived basic cystatin is a protein obtainable by a method comprising (i) passing skimmed milk through an S-sepharose column; (ii) eluting a fraction from the column using a linear concentration gradient of 0.1 to 1.0 M sodium chloride; (iii) heating the eluted fraction to 90° C.; (iv) centrifuging the eluted fraction to remove precipitates, thereby creating a first fraction; (v) fractionating the first fraction using MonoS ion exchange chromatography, thereby creating a second fraction; (vi) fractionating the second fraction using MonoQ ion exchange chromatography, Superose 12 gel filtration chromatography using an HPLC system, hydroxyapatite chromatography, and C4 reverse phase chromatography using an HPLC system, or a method comprising (I) heating a 5% milk whey protein solution to 90° C.; (II) centrifuging the solution to remove precipitates, thereby creating a first fraction; (III) passing the first fraction through a column filled with a carrier wherein carboxymethylated papain is bound to Tresyl-Toyopearl and equilibrated with a 0.5 M sodium chloride solution; (IV) washing the column with a 0.5 M sodium chloride solution and then a 0.5 M sodium chloride solution containing 0.1% Tween 20; (V) eluting cysteine protease with a 20 mM acetic acid-0.5M sodium chloride solution; (VI) neutralizing the eluted fraction with a 1 M sodium hydroxide solution, thereby creating a second fraction; and (VII) fractionating the second fraction on MonoS anion exchange chromatography, hydroxy apatite chromatography, and C4 reverse phase chromatography using an HPLC system.

* * * * *